United States Patent
Chen et al.

(10) Patent No.: US 9,358,525 B2
(45) Date of Patent: Jun. 7, 2016

(54) NO$_x$ STORAGE MATERIALS FOR SENSOR APPLICATIONS

(75) Inventors: Hai-Ying Chen, Conshohocken, PA (US); Shadab Mulla, King of Prussia, PA (US); Todd Howard Ballinger, Downingtown, PA (US)

(73) Assignee: Johnson Matthey Public Limited Company, London (GB)

( * ) Notice: Subject to any disclaimer, the term of this patent is extended or adjusted under 35 U.S.C. 154(b) by 1505 days.

(21) Appl. No.: 12/630,344

(22) Filed: Dec. 3, 2009

(65) Prior Publication Data

US 2010/0146935 A1 Jun. 17, 2010

Related U.S. Application Data

(60) Provisional application No. 61/119,860, filed on Dec. 4, 2008.

(51) Int. Cl.
| | |
|---|---|
| *B01J 23/58* | (2006.01) |
| *B01D 53/30* | (2006.01) |
| *B01D 53/94* | (2006.01) |
| *B01J 23/656* | (2006.01) |
| *B01J 23/96* | (2006.01) |
| *B01J 37/02* | (2006.01) |
| *G01N 27/12* | (2006.01) |
| *G01N 33/00* | (2006.01) |

(52) U.S. Cl.
CPC .............. *B01J 23/58* (2013.01); *B01D 53/30* (2013.01); *B01D 53/9422* (2013.01); *B01J 23/6562* (2013.01); *B01J 23/96* (2013.01); *B01J 37/0215* (2013.01); *G01N 27/125* (2013.01); *B01D 2255/102* (2013.01); *B01D 2255/2022* (2013.01); *B01D 2255/2061* (2013.01); *B01D 2255/2063* (2013.01); *B01D 2255/2066* (2013.01); *B01D 2255/2068* (2013.01); *B01D 2255/2073* (2013.01); *B01D 2255/2092* (2013.01); *B01D 2255/91* (2013.01); *G01N 33/0037* (2013.01)

(58) Field of Classification Search
None
See application file for complete search history.

(56) References Cited

U.S. PATENT DOCUMENTS

| | | | |
|---|---|---|---|
| 5,939,037 A | 8/1999 | Hepburn | |
| 6,240,722 B1 | 6/2001 | Busch et al. | |
| 6,833,272 B1 | 12/2004 | Binder et al. | |
| 7,097,875 B2 * | 8/2006 | Clyde et al. | 427/115 |
| 2002/0014107 A1 | 2/2002 | Moos et al. | |
| 2002/0124551 A1 | 9/2002 | Birkhofer et al. | |
| 2003/0011374 A1 | 1/2003 | Seipler et al. | |
| 2003/0091499 A1 | 5/2003 | Becue | |
| 2003/0124035 A1 * | 7/2003 | Bert et al. | 422/171 |
| 2004/0206067 A1 | 10/2004 | Birkhofer et al. | |
| 2007/0080075 A1 * | 4/2007 | Wang et al. | 205/781 |
| 2009/0071229 A1 * | 3/2009 | Grimshaw | 73/23.31 |
| 2010/0193356 A1 * | 8/2010 | Wahl et al. | 204/432 |

FOREIGN PATENT DOCUMENTS

| | | | |
|---|---|---|---|
| EP | 1358933 | | 11/2003 |
| WO | WO-98/10272 A1 | | 3/1998 |
| WO | WO-02/22241 A1 | | 3/2002 |
| WO | WO-02/095199 A1 | | 11/2002 |
| WO | 2005015191 | | 2/2005 |
| WO | 2007068587 | * | 6/2007 |

OTHER PUBLICATIONS

International Search Report dated May 21, 2010, application No. PCT/GB2009/051653.
Moos et al., "Sensor for Directly Determining the State of a NOx Storage Catalyst," *SAE Technical Paper Series*, Paper No. 2008-1-0447, presented at the SAE International 2008 World Congress in Detroit, Michigan, Apr. 14-17, 2008.

* cited by examiner

*Primary Examiner* — Melvin C Mayes
*Assistant Examiner* — Sheng H Davis
(74) *Attorney, Agent, or Firm* — Jimmie D. Johnson

(57) ABSTRACT

A NO$_x$ storage material comprises a support, a potassium salt impregnated on the support, the potassium impregnated on the support is promoted with a platinum group metal, and wherein the NO$_x$ storage material has an electrical property which changes based on the amount of NO$_x$ loading on the NO$_x$ storage material. An apparatus for direct NO$_x$ measurement includes a sensor coated with the NO$_x$ storage material. A method of determining NO$_x$ flux in a NO$_x$ containing gas comprises exposing the gas to the apparatus and converting a signal developed by the apparatus to a signal representative of the NO$_x$ flux.

6 Claims, No Drawings

$NO_x$ STORAGE MATERIALS FOR SENSOR APPLICATIONS

CROSS-REFERENCE TO RELATED APPLICATIONS

This application claims priority of U.S. Provisional Patent Application No. 61/119,860, filed Dec. 4, 2008, which is incorporated herein by reference.

FIELD OF THE INVENTION

The invention relates to a nitrogen oxide ($NO_x$) storage material useful for $NO_x$ sensors for direct $NO_x$ measurements.

BACKGROUND OF THE INVENTION $NO_x$ emissions from automobiles, fossil fuel-fired power stations and industrial plants, and the like, need to be monitored to control and maintain low $NO_x$ emission levels to meet stringent $NO_x$ emission standards. For gasoline engines that run at a stoichiometric mixture of air and fuel, the engine out $NO_x$ emissions are generally controlled by three-way-catalysts (TWCs), which convert CO, hydrocarbons, and $NO_x$ simultaneously with high efficiency. For internal combustion engines that burn a lean mixture of fuel and air, however, the conventional TWCs do not reduce $NO_x$ efficiently. For lean burn $NO_x$ emission control, several other technologies are being investigated including lean $NO_x$ trap (LNT) aftertreatment systems and selective catalytic reduction (SCR) of $NO_x$ with urea. In an LNT system, also called a $NO_x$ adsorber catalyst (NAC), $NO_x$ is trapped on the catalyst during normal lean operations, and when the LNT reaches a certain $NO_x$ storage level, the engine is operated rich for a short period of time to cause the absorbed $NO_x$ to desorb from the catalyst surface. The rich exhaust gases contain CO and unburned hydrocarbons that reduce $NO_x$ to $N_2$. In a urea-SCR system, a controlled amount of urea is injected to the exhaust which decomposes to form $NH_3$, and $NO_x$ is selectively reduced by the $NH_3$. In both LNT and SCR systems, accurately monitoring $NO_x$ concentration and $NO_x$ flux is important in order to achieve high $NO_x$ reduction efficiency.

Some commercially available $NO_x$ sensors use $O_2$ sensing technologies and are not direct $NO_x$ measurement devices. These $O_2$ sensing technologies suffer from problems associated with interference from other compounds that may exist in the exhaust gases. Therefore, new technologies for direct $NO_x$ measurements are preferable for more accurate and precise monitoring of $NO_x$ concentration and $NO_x$ flux. One approach is to apply catalytic components onto sensors that consist of interdigital electrodes, a heater, and temperature sensors. By measuring the change of the electrical properties (e.g. electrical impedances) of the catalytic components, it is feasible to directly gauge the $NO_x$ loading status on the catalyst. For example, WO9810272A1 describes a method for determining the $NO_x$ storage load of a $NO_x$ storage catalyst by using a monitoring sensor where the storage material forms the sensitive element in the sensor. U.S. Pat. No. 6,833,272 describes a sensor for determining the storage-state of an $NH_3$-adsorbing SCR catalyst on the basis of sensing the electrical impedance of the SCR catalyst. SAE 2008-01-0447 discusses the monitoring of the $NO_x$ storage and reduction process, degree of $NO_x$ loading, thermal aging and sulphur poisoning via the measurement of electrical impedance of NAC coated sensors inserted in the NAC catalyst.

One of the $NO_x$ storage components reported in the literature (e.g. SAE 2008-01-0447) is a barium-based formulation, containing noble metals and ceria. It appears that the response of its electrical property to $NO_x$ loading was not strong and quickly approached a plateau. For example, at 350° C., the impedance only changed by about 6% and reached a plateau in about 2 minutes with a gas concentration of 0.055% NO (see FIG. 3 in SAE 2008-01-0447). In addition, the barium-based $NO_x$ storage material suffered from low $NO_x$ storage capacity at high temperatures.

SUMMARY OF THE INVENTION

The present invention is directed to the use of a potassium-based $NO_x$ storage component that has a strong response in the material's electrical property to the $NO_x$ loading process and a superior high temperature storage capacity, for example, as compared to the ones reported in the literature (e.g., SAE 2008-01-0447).

According to an embodiment of the present invention, a $NO_x$ storage material comprises a support and a potassium salt impregnated on the support. The potassium impregnated on the support is promoted with a platinum group metal. The $NO_x$ storage material has an electrical property which changes based on an amount of $NO_x$ loading on the $NO_x$ storage material.

According to another embodiment of the present invention, an apparatus for direct $NO_x$ measurement comprises a $NO_x$ storage material comprising a support and a potassium salt impregnated on the support. The potassium impregnated on the support is promoted with a platinum group metal. The $NO_x$ storage material has an electrical property which changes based on an amount of $NO_x$ loading on the $NO_x$ storage material. A sensor coated with the $NO_x$ storage material provides a signal in response to the electrical property.

According to another embodiment of the present invention, a composition for application to a sensor and, upon drying and calcining, for storing $NO_x$ comprises an aqueous mixture of a support, a potassium salt, and a salt of a platinum group metal, wherein the composition, upon drying and calcining, has an electrical property which changes based on an amount of $NO_x$ loading on the dried composition.

According to another embodiment of the present invention, a method of determining $NO_x$ flux in a $NO_x$ containing exhaust gas comprises exposing the $NO_x$ containing exhaust gas to an apparatus comprising: (1) a $NO_x$ storage material and (2) a sensor coated with the $NO_x$ storage material for providing a first signal in response to an electrical property; and converting the first signal to a second signal representative of the $NO_x$ flux in the $NO_x$ containing exhaust gas. The $NO_x$ storage material comprises a support and a potassium salt impregnated on the support. The potassium impregnated on the support is promoted with a platinum group metal. The $NO_x$ storage material has an electrical property which changes based on an amount of $NO_x$ loading on the $NO_x$ storage material.

DETAILED DESCRIPTION OF THE INVENTION

Aspects of the present invention include a $NO_x$ storage material; an apparatus for direct $NO_x$ measurement; a composition for application to a sensor and, upon drying and calcining, for storing $NO_x$; and a method for determining $NO_x$ flux in a $NO_x$ containing exhaust gas.

In a first embodiment of the present invention, a $NO_x$ storage material comprises a support and a potassium salt impregnated on the support. The potassium impregnated on the support is promoted with a platinum group metal. The $NO_x$ storage material has an electrical property which changes based on an amount of $NO_x$ loading on the $NO_x$ storage material. Accordingly, in one aspect, the present invention provides a potassium-based $NO_x$ storage component that has a strong response in the material's electrical property to the $NO_x$ loading process and also has superior high temperature storage capacity compared to typical barium-based $NO_x$ storage components.

The $NO_x$ storage material comprises a support. The support may include high surface area support materials, which are stable at high exhaust gas temperatures. For example, temperatures may reach up to 700° C. to 800° C. Any support may be used, but particularly suitable supports may include alumina, silica, titania, zirconia, ceria, and mixtures thereof. The support material may also be stabilized. Stabilizers may be selected from zirconium (Zr), lanthanum (La), aluminum (Al), yttrium (Y), praseodymium (Pr), neodymium (Nd), an oxide thereof, a composite oxide or mixed oxide of any two or more thereof, or at least one alkaline earth metal, e.g., barium (Ba). In one embodiment, the support material is alumina ($Al_2O_3$), and more preferably is lanthanum-stabilized alumina.

A potassium precursor may be impregnated on the support. The potassium precursor may start as an oxide, carbonate, or hydroxide of potassium and manganese and form the end product upon calcining and exposure to air. Upon exposure to the $NO_x$ containing exhaust gases, however, the potassium may be eventually transformed into nitrates. Thus, the potassium upon storing the $NO_x$ from the $NO_x$ containing exhaust gas forms nitrates which provides a strong change in the electrical property based on the amount of $NO_x$ loading. In particular, a manganese promoted potassium is especially suitable to maintain its durability and dispersion. Manganese may be introduced together with potassium using potassium permanganate as a precursor. Without wishing to be bound to a particular theory, it appears that the manganese stabilizes the potassium, prevents thermal sintering, and promotes nitrate formation.

The potassium permanganate impregnated on the support is then promoted with a platinum group metal. As used herein, "promoter" or "promoted" are understood to mean a substance that when added to a catalyst, increases the activity of the catalyst. The platinum group metal may be any suitable platinum group metal such as palladium, platinum, iridium, rhodium, ruthenium, or osmium. In one embodiment, the platinum group metal is platinum, and more specifically, may be added in the form of a salt such as platinum nitrate or tetra-amine platinum acetate. The platinum also acts as an oxidation catalyst for NO to $NO_2$, and for $NO_2$ to nitrite and nitrate.

In preparing the $NO_x$ storage material, a washcoat may be prepared. A support may or may not be milled. At least one support, for example La-stabilized alumina, may be milled to a particle size of less than about 20 μm or more particularly less than 15 μm. The support or supports may be formed into an aqueous slurry. The platinum group metal, for example a platinum salt solution, may be added to the slurry. The potassium salt may then be blended into the mixture. Next, a substrate, e.g., a sensor comprising interdigital electrodes, a heater, and temperature sensors, may be coated by applying the slurry as a thin uniform film or layer. The coating may be applied using any method known in the art such as by applying with a spatula, spray coating, print screening, painting, or any other suitable coating techniques generally know in the art. Only a small area of the substrate needs to be coated, i.e., the entire substrate need not be coated. The coating is then dried. The coating may be dried under ambient conditions or other suitable conditions. The substrate is then calcined. The substrate may be calcined, for example, at 500° C. for about 2 hours.

The $NO_x$ storage material has an electrical property which changes based on an amount of $NO_x$ loading on the $NO_x$ storage material. By measuring the change of an electrical property of the catalytic components, the $NO_x$ loading status on the catalyst may be directly gauged. The electrical properties of the $NO_x$ storage material may include resistance, conductivity, capacitance, or permittivity. In one embodiment, the preferred electrical property is impedance.

Electrical impedance may be represented in a two-dimensional coordinate system and be defined as the complex impedance. The quantities may include: ohmic resistance and capacity; ohmic resistance and amount of the impedance; amount and real part of the impedance; or amount and phase of the impedance. The complex electrical impedance Z may be defined as the sum of the real part Re[Z] and the imaginary part Im[Z] of the complex impedance Z. Electrical impedance Z changes with the applied measuring frequency, and therefore, the frequency should be maintained.

As used herein, "$NO_x$ loading" is understood to mean the amount of $NO_x$ adsorbed onto the $NO_x$ storage material. Thus, the loading of $NO_x$ onto the $NO_x$ storage material is cumulative. When the $NO_x$ storage material is introduced or placed into a $NO_x$ containing gas stream, for example, in the exhaust stream of a lean mix engine or a diesel engine, the storage material is increasingly charged or loaded with $NO_x$. When there is no $NO_x$ in the gas stream or the material is removed from a $NO_x$ containing gas stream, $NO_x$ loading does not occur. Additionally, the composition of the storage material is able to both store and release $NO_x$. For example, continued exposure to a $NO_x$ containing gas stream causes more $NO_x$ to be stored on the $NO_x$ storage material, and the $NO_x$ loading is greater. Alternatively, when $NO_x$ is released from the material (e.g., regenerated), the $NO_x$ loading would be lower or none. The composition would then be able to once again accumulate $NO_x$ loading. An amount of $NO_x$ loading then correlates to an electrical property, namely impedance. The $NO_x$ loading is generally proportional to the output for an impedance value. A direct (linear) proportionality between the $NO_x$ loading and the output for an impedance value is especially advantageous.

In another embodiment of the present invention, an apparatus for direct $NO_x$ measurement comprises a $NO_x$ storage material comprising a support and a potassium salt impregnated on the support. The potassium impregnated on the support is promoted with a platinum group metal. The $NO_x$ storage material has an electrical property which changes based on an amount of $NO_x$ loading on the $NO_x$ storage material, and a sensor coated with the $NO_x$ storage material provides a signal in response to the electrical property.

A sensor may be coated with the $NO_x$ storage material and the $NO_x$ storage material forms the sensitive element of the sensor. The sensor may include an electrically conductive substrate, interdigital electrodes, heater(s), and temperature sensor(s). An appropriate sensor may include the sensors defined in SAE Paper 2008-01-0447, U.S. Publication No. 2002/0014107, or U.S. Pat. No. 6,240,722, all of which are herein incorporated by reference. Of course, these sensors would be altered to use the $NO_x$ storage material described herein as the sensitive element. Any appropriate sensor able to produce the appropriate signal in response to $NO_x$ loading on the $NO_x$ storage material would be suitable for the present invention. The sensor and related components should also be durable and able to withstand the high temperatures typically present in exhaust gas.

The $NO_x$ storage material may produce an electrical property in response to $NO_x$ loading which is linear, quasi-linear, pseudo-linear, curved, etc. In particular, the $NO_x$ storage material may produce a linear response of impedance to $NO_x$ loading, at least over a region of the impedance-$NO_x$ exposure curve having zero $NO_x$ loading to some degree of saturation. An impedance-$NO_x$ exposure curve shows impedance on the y-axis with varying $NO_x$ exposure as a function of time on the x-axis. $NO_x$ exposure is understood to have a direct proportional relationship with $NO_x$ loading on the $NO_x$ storage material. As used herein, "linear response" or "respond linearly" is understood to mean a function where the results plotted on a graph form a substantially straight line. Thus, a linear polynomial of the electrical property would show the slope or gradient as a substantially straight line, e.g., a negative slope if the line is sloping down to the right. In an exemplary embodiment, a steeper slope in the negative direction would correspond to an increase in sensitivity to changes in $NO_x$ loading. In some embodiments, the steepest and most linear portion of the curve can be found when loading begins from an unsaturated (e.g., zero loading) $NO_x$ storage material. While it is preferable to operate in the region of the curve which is substantially linear and has a steep slope, it is possible to operate in a region which is no longer substantially linear or has a lesser slope, but these regions would have a lower sensitivity to changes in $NO_x$ loading. As can be appreciated, as the slope of the curve approaches zero the accuracy of the measurements may decrease significantly.

The $NO_x$ storage material may produce a sustained response of impedance when $NO_x$ loading is maintained. As used herein, "sustained response" is understood to mean a non-changing response where the signal holds at the same value for the electrical property, e.g., a horizontal line with a slope of zero. This would occur, for example, when there is zero $NO_x$ in the gas stream or if the material were removed from the gas stream. The result of a sustained response is that the $NO_x$ loading would not be changing and would be maintained at the same value. Thus, excellent stability of the material is evidenced by removing $NO_x$ from the gas stream where the electrical properties of the material do not change.

As the electrical property has a higher signal intensity, a greater range in the change of impedance results in a more accurate value of $NO_x$ loading. For example, when the material is first exposed to $NO_x$ in the gas stream, the change in impedance may be up to 60% for a given amount of exposure to $NO_x$, which indicates a very high sensitivity to $NO_x$ loading as compared to other known materials for such applications which may typically show only 6-10% change in impedance for similar exposure to $NO_x$, such as the barium-based material from SAE Paper 2008-01-0447. Thus, as compared to other known sensors, the $NO_x$ material of the present invention provides a larger response in the electrical property for a given change in $NO_x$ loading.

$NO_x$ loading, $NO_x$ flux, and $NO_x$ concentration may be all used to describe the amount of $NO_x$ stored on the $NO_x$ storage material. Unlike previous $O_2$ sensing technologies, the $NO_x$ storage material of the present invention allows the $NO_x$ loading or $NO_x$ flux to be directly measured. $NO_x$ is typically measured for emissions standards in grams per mile. As used herein, "$NO_x$ flux" is understood to mean a cumulative amount of adsorbed $NO_x$ in a given time period on the $NO_x$ storage material. When the $NO_x$ storage material has low or no $NO_x$ coverage, it adsorbs $NO_x$ from the gas stream with 100% efficiency. Hence, "$NO_x$ flux" may also be understood as an integral of the amount of $NO_x$ in the gas stream over a given period of time. Thus, $NO_x$ flux can be calculated by integrating the $NO_x$ concentration in a $NO_x$ containing gas stream multiplied by the gas flow rate over a period of time. $NO_x$ concentrations may be understood as not only the concentration of $NO_x$ in the gas stream, but also the cumulative amount of $NO_x$ on the $NO_x$ storage material divided by the amount of the $NO_x$ storage material. As used herein, "$NO_x$ concentration in a $NO_x$ containing exhaust gas" should be construed as the former, a varying or constant concentration of $NO_x$ in the gas stream. The $NO_x$ storage material is advantageous in that it is able to measure $NO_x$ precisely at very low levels, for example, as low as in the less than 1 part per million (ppm) range.

In another embodiment of the present invention, a composition for application to a sensor and, upon drying and calcining, for storing $NO_x$, comprises an aqueous mixture of a support, a potassium salt, and a salt of a platinum group metal, wherein the composition, upon drying and calcining, has an electrical property which changes based on the amount of $NO_x$ loading on the dried composition. The composition is applied to a substrate/sensor and may be dried and calcined using the process described above. The composition adheres to the substrate or sensor for use. The composition comprises an aqueous mixture of a support, a potassium salt, and a salt of a platinum group metal. The support may be alumina, the potassium salt may be potassium permanganate, and the salt of the platinum group metal may be a platinum salt, namely platinum nitrate. Other salts may also be used such as tetraamine platinum acetate or acetates of potassium and manganese.

In another embodiment of the present invention, a method of determining $NO_x$ flux in a $NO_x$ containing exhaust gas comprises exposing the $NO_x$ containing exhaust gas to an apparatus comprising: (1) a $NO_x$ storage material and (2) a sensor coated with the $NO_x$ storage material for providing a first signal in response to the electrical property; and converting the first signal to a second signal representative of the $NO_x$ flux in the $NO_x$ containing exhaust gas. The $NO_x$ storage material comprises a support and a potassium salt impregnated on the support. The potassium impregnated on the support is promoted with a platinum group metal. The $NO_x$ storage material has an electrical property which changes based on the amount of $NO_x$ loading on the $NO_x$ storage material.

In the method of determining $NO_x$ flux in a $NO_x$ containing exhaust gas, an apparatus is used comprising the $NO_x$ storage material described above and a sensor coated with the $NO_x$ storage material. The apparatus is exposed to a $NO_x$ containing exhaust gas. The material should be coated on the sensor in such a way that the $NO_x$ storage material may be readily reached by the exhaust gas stream. As the $NO_x$ storage material has an electrical property which changes based on the amount of $NO_x$ loading on the $NO_x$ storage material, the sensor may provide a first signal in response to the electrical property. The first signal may be a value representing the electrical property, such as impedance. As discussed above, the electrical property based on the amount of the $NO_x$ loading may be selected from impedance, resistance, conductivity, or capacitance, for example. The sensor converts the first signal to a second signal that represents the $NO_x$ flux in the $NO_x$ containing exhaust gas. Thus, a relationship correlating the $NO_x$ loading or the $NO_x$ flux to the value or values for impedance, may allow value(s) for impedance to represent a known concentration of $NO_x$ in the exhaust gas over a given period of time. As previously discussed, the electrical impedance may respond linearly to the amount of the $NO_x$ loading on the $NO_x$ storage material, at least over a region of the impedance-$NO_x$ exposure curve.

The NO$_x$ storage material may be repeatedly regenerated in use. Regeneration is important in maintaining the NO$_x$ loading/electrical property output in a linear region. When the NO$_x$ loading reaches a certain level, the electrical property, for example, impedance, will no longer be responding in a linear fashion. Without wishing to be bound to a particular theory, it is believed that as the material gets close to saturation, an equilibrium may be reached which causes a deviation from linearity. For example, the following equilibrium may be reached:

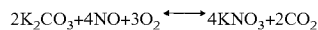

In order to regenerate, oxygen may be removed and/or hydrogen or carbon monoxide or hydrocarbons may be added to the feed to recover K$_2$CO$_3$. The equilibrium is also a function of temperature. Therefore, the NO$_x$ storage material may be regenerated, for example, by heating or with a reductant (reducing agent). Furthermore, when the NO$_x$ storage material is heated to higher temperatures, regeneration may occur faster. As described above for the sensor, the sensor preferably contains a heater to allow for such regeneration by heating. Therefore, when the NO$_x$ loading reaches a certain level and the material is no longer responding in a linear manner, the NO$_x$ storage material may be regenerated. The electrical property values will then return to the linear response region, and the NO$_x$ storage material may be used again.

The NO$_x$ storage material of the present invention has the ability to be regenerated numerous times and still maintain its desired linear and steep response prior to reaching the above described equilibrium, at least over a region of the impedance-NO$_x$ exposure curve. The electrical property responds with the greatest degree of linearity and with the most sensitivity (i.e., with the steepest slope) when the catalyst is clean, e.g., when there is no NO$_x$ loading because the catalyst is new or was just regenerated. The extent of linearity deteriorates to a point where the response is no longer linear as the catalyst is used, e.g., as NO$_x$ accumulates on the NO$_x$ storage material.

An absolute value or change of the NO$_x$ loading could be determined through a calibration with a known concentration of NO$_x$, for a given time, and at a given flow rate. A correlation may then be developed from the calibration data which would show a proportional relationship between the amount of NO$_x$ exposure, the amount of NO$_x$ adsorbed, and the change in the electrical property. A correlation may take the form of a NO$_x$ loading-impedance curve where NO$_x$ loading is the dependent variable. The NO$_x$ loading-impedance curve would have impedance on the x-axis and NO$_x$ loading on the y-axis. Similar to the impedance-NO$_x$ exposure curve, the NO$_x$ loading-impedance curve may have a linear, quasi-linear, pseudo-linear, or curved relationship. Preferably, a linear relationship would be best to show the direct proportionality between the impedance values or change in impedance and the NO$_x$ loading values or change in NO$_x$ loading. Moreover, as the shape of the curve departs from linearity, the calibration curve may become more complex to utilize in practice. In sum, a change in the electrical property may be correlated to a certain degree of cumulative amount of NO$_x$ loading change.

This correlation would allow one of ordinary skill in the art to identify an absolute value or range of NO$_x$ loading or NO$_x$ flux based on a given impedance measurement or change in impedance (the NO$_x$ loading-impedance curve). In operation, where the response on the impedance-NO$_x$ exposure curve is no longer linear, e.g., demonstrating some degree of saturation of the NO$_x$ storage material, the NO$_x$ storage material should be regenerated to return the response to the linear region. By maintaining the NO$_x$ storage material in the linear region during operation, the amount of NO$_x$ loading or NO$_x$ flux can best be determined while in use, e.g., for direct NO$_x$ measurements of NO$_x$ emissions.

In at least one aspect, the present invention provides higher NO$_x$ storage, better high temperature stability, and better stability in exhaust gas compared to other known materials for such applications. Thus, the NO$_x$ storage materials according to embodiments of the present invention are useful for direct NO$_x$ measurements to monitor, control, and maintain low NO$_x$ emission levels from automobiles, fossil fuel-fired power stations, industrial plants, and the like.

EXAMPLES

The following examples are included to more clearly demonstrate the overall nature of the present invention. In particular, Examples 1-4 describe exemplary methods for making a coated sensor of the present invention which has at a least a region of the impedance-NO$_x$ exposure curve which is linear and has a sufficiently steep slope suitable for accurately determining NO$_x$ loading.

In Example 1, an aqueous slurry of alumina stabilized with 3.5 wt % lanthanum was mixed with tetra-amine platinum acetate such that the finished material contained a total of 0.77 wt % platinum, based on the total weight of the material. Potassium acetate was then added to obtain a potassium loading of 7.26 wt % based on the total weight of the material. Next, the substrate was coated by applying the slurry as a thin uniform film or layer using a spatula on the desired portion of the substrate (the substrate may be a portion of the sensor). The coating was dried under ambient conditions and the substrate was calcined at 500° C. for 2 hours.

In Example 2, Example 1 was repeated but additionally, manganese acetate was added following the potassium acetate addition to obtain a manganese loading of 10.25 wt % based on the total weight of the material. The manganese promoted slurry was then applied to the desired portion of the substrate as a thin uniform film or layer using a spatula. The coating was dried under ambient conditions and the substrate was calcined at 500° C. for 2 hours.

In Example 3, contrary to Example 2, the potassium and manganese acetate salts were dissolved together in water and the solution was then added to the platinum containing alumina slurry. The slurry was then applied to the desired portion of the substrate as a thin uniform film or layer using a spatula. The coating was dried under ambient conditions and the substrate was calcined at 500° C. for 2 hours.

In Example 4, an aqueous slurry of alumina stabilized with 3.5 wt % lanthanum was mixed with platinum nitrate such that the finished material contained a total of 0.77 wt % platinum, based on the total weight of the material. Potassium permanganate was then added to get a potassium loading of 7.26 wt % based on the total weight of the material. Next, the substrate was coated by applying the slurry as a thin uniform film or layer using a spatula on the desired portion of the substrate (the substrate may be a portion of the sensor). The coating was dried under ambient conditions and the substrate was calcined at 500° C. for 2 hours.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A $NO_x$ storage material comprising: a support; and potassium permaganate impregnated on the support, wherein the potassium impregnated on the support is promoted with a platinum group metal, and wherein the $NO_x$ storage material has an electrical property which changes based on an amount of $NO_x$ loading on the $NO_x$ storage material, wherein the platinum group metal is selected from the group consisting of palladium, platinum, iridium, rhodium, ruthenium, and osmium.

2. The $NO_x$ storage material according to claim 1, wherein the platinum group metal platinum.

3. The $NO_x$ storage material according to claim 1, wherein the support is selected from the group consisting of alumina, silica, titania, zirconia, ceria, and mixtures thereof.

4. The $NO_x$ storage material according to claim 1, wherein the support is alumina.

5. The NO storage material according to claim 4, wherein the support is lanthanum-stabilized alumina.

6. The NO storage material according to claim 1, wherein the electrical property is impedance.

* * * * *